United States Patent
Austin et al.

(10) Patent No.: US 6,921,532 B1
(45) Date of Patent: Jul. 26, 2005

(54) BIOLOGICAL BIOADHESIVE COMPOSITION AND METHODS OF PREPARATION AND USE

(75) Inventors: Sam L. Austin, Boise, ID (US); Thomas E. Davis, Caldwell, ID (US)

(73) Assignee: Spinal Restoration, Inc., Austin, TX (US)

( * ) Notice: Subject to any disclaimer, the term of this patent is extended or adjusted under 35 U.S.C. 154(b) by 54 days.

(21) Appl. No.: 10/280,133

(22) Filed: Oct. 22, 2002

Related U.S. Application Data

(63) Continuation-in-part of application No. 09/888,310, filed on Jun. 22, 2001, now Pat. No. 6,468,527.
(60) Provisional application No. 60/213,806, filed on Jun. 22, 2000.

(51) Int. Cl.[7] .............................................. A61K 38/48
(52) U.S. Cl. ...................... 424/94.64; 424/94.1; 514/2; 514/169
(58) Field of Search ........................... 424/94.1, 94.64; 514/2, 169, 167, 168, 170–82

(56) References Cited

U.S. PATENT DOCUMENTS

| | | | |
|---|---|---|---|
| 2,533,004 A | 12/1950 | Ferry et al. ................... | 260/112 |
| 3,089,815 A | 5/1963 | Lieb et al. ..................... | 167/58 |
| 4,359,049 A | 11/1982 | Redl et al. ............. | 128/218 PA |

(Continued)

FOREIGN PATENT DOCUMENTS

| | | | | |
|---|---|---|---|---|
| DE | 3037270 | 5/1982 | ............ | A61L/15/04 |
| EP | 0 068 149 | 5/1982 | ............ | A61L/15/04 |
| WO | WO 81/00516 | 5/1981 | ............ | A61K/9/18 |
| WO | WO92/22312 | 12/1992 | | |
| WO | WO 94/20133 | 9/1994 | ......... | A61K/37/547 |
| WO | WO 96/17633 | 3/1996 | ............ | A61L/25/00 |
| WO | WO97/42986 | 11/1997 | | |

OTHER PUBLICATIONS

US 6,645,204, 11/2003, Sharkey et al. (withdrawn)
Abstract: Yagita, T., *Agent for Controlling Formation of Cheloid at Excision Site for Inflammation Bowel Disease*. . . ,Database WPI, Section Ch, Week 199716, Derwent Publications Ltd., London, GB XP002182938, Feb. 10, 1997.
Abstract: Sumitomo Cement Co., *Sustained Release Agent for Treatment of Osteomyelitis* . . . , Database WPI, Section Ch, Week 199306, Derwent Publications Ltd., London, GB XP002182939, Jan. 8, 1993.

(Continued)

*Primary Examiner*—Thurman K. Page
*Assistant Examiner*—Konata M. George
(74) *Attorney, Agent, or Firm*—O'Keefe, Egan & Peterman

(57) ABSTRACT

The present invention relates generally to the preparation and use of biological tissue adhesives which rely on combining fibrinogen and thrombin. More particularly, the present invention relates to a method of preparing a fibrin sealant whereby said sealant is formed by reconstituting the fibrinogen or the thrombin component in the presence of biological and/or non-biological agents such as drugs, chemicals, and proteins. Preferably, these agents are introduced in solution, such as for example, a corticosteroid-containing solution like a betamethasone solution containing betamethasone acetate or betamethasone sodium phosphate; a triamicinolone solution; or a methylprednisolone solution. These solutions may be substituted for, or provided as a complement to, other solutions that are typically used in the preparation of fibrin sealants such as, for example, calcium chloride. The invention further relates to a novel method of using the improved fibrin sealant whereby the sealant and accompanying agent(s) are delivered directly to a critical site within the body and sealed in place due to the bio-static quality of the sealant. This provides therapeutic value to patients through prolonged presence, and optionally time-released delivery, of the specific agent(s) at the critical site.

48 Claims, 1 Drawing Sheet

U.S. PATENT DOCUMENTS

| | | |
|---|---|---|
| 4,393,041 A | 7/1983 | Brown et al. ............... 424/19 |
| 4,427,650 A | 1/1984 | Stroetmann ................ 424/46 |
| 4,442,655 A | 4/1984 | Stroetmann ................ 53/428 |
| 4,619,913 A | 10/1986 | Luck et al. ............... 514/131 |
| RE33,375 E | 10/1990 | Luck et al. ................. 514/2 |
| 5,124,155 A | 6/1992 | Reich ....................... 424/428 |
| 5,264,446 A | 11/1993 | Hegasy et al. ............ 514/356 |
| 5,290,552 A | 3/1994 | Sierra et al. ........... 424/94.64 |
| 5,643,192 A | 7/1997 | Hirsh et al. ................... 604/4 |
| 5,651,982 A | 7/1997 | Marx ....................... 424/450 |
| 5,702,715 A | 12/1997 | Nikolaychik et al. ...... 424/402 |
| 5,925,738 A | 7/1999 | Miekka et al. ............. 530/380 |
| 5,962,420 A | 10/1999 | Edwardson et al. ......... 514/21 |
| 5,980,504 A | 11/1999 | Sharkey et al. ........... 604/510 |
| 5,980,866 A | 11/1999 | Uchida et al. ............... 424/45 |
| 6,007,570 A | 12/1999 | Sharkey et al. ............. 607/96 |
| 6,007,811 A | 12/1999 | Sawyer et al. .......... 424/94.64 |
| 6,054,122 A | 4/2000 | MacPhee et al. ......... 424/94.4 |
| 6,073,051 A | 6/2000 | Sharkey et al. ............. 607/99 |
| 6,117,425 A | 9/2000 | MacPhee et al. ........ 424/94.64 |
| 6,122,549 A | 9/2000 | Sharkey et al. ............. 607/99 |
| 6,124,273 A | 9/2000 | Drohan et al. ............. 514/55 |
| 6,126,682 A | 10/2000 | Sharkey et al. ............. 607/99 |
| 6,183,518 B1 | 2/2001 | Ross et al. ............. 623/17.16 |
| 6,197,325 B1 | 3/2001 | MacPhee et al. .......... 424/426 |
| 6,258,086 B1 | 7/2001 | Ashley et al. ............... 606/41 |
| 6,261,311 B1 | 7/2001 | Sharkey et al. ............. 607/96 |
| 6,320,029 B1 | 11/2001 | Miekka et al. ............. 530/380 |
| 6,428,576 B1 | 8/2002 | Haldimann ............. 623/17.16 |
| 6,468,527 B2 * | 10/2002 | Austin et al. ........... 424/94.64 |
| 6,517,568 B1 | 2/2003 | Sharkey et al. ............. 607/96 |
| 6,547,810 B1 | 4/2003 | Sharkey et al. ............. 607/96 |
| 6,638,276 B2 | 4/2003 | Sharkey et al. ............. 606/41 |
| 6,559,119 B1 | 5/2003 | Burgess et al. ............... 514/2 |
| RE38,431 E | 2/2004 | Miekka et al. ............. 530/380 |
| 6,726,685 B2 | 4/2004 | To et al. ...................... 606/50 |
| 6,733,496 B2 | 5/2004 | Sharkey et al. ............. 606/41 |
| 6,749,605 B2 | 6/2004 | Ashley et al. ............... 606/41 |
| 6,762,336 B1 | 7/2004 | MacPhee et al. ........... 602/48 |
| 6,767,347 B2 | 7/2004 | Sharkey et al. ............. 606/41 |
| 2003/0181964 A1 | 9/2003 | Sharkey et al. ............. 607/96 |
| 2004/0111136 A1 | 6/2004 | Sharkey et al. ............. 607/99 |
| 2004/0193151 A1 | 9/2004 | To et al. ...................... 606/41 |

OTHER PUBLICATIONS

J. Rousou, et al., "Randomized Clinical Trial of Fibrin Sealant in Cardiac Surgery Patients Undergoing Resternotomy . . .", *Journal of Thoracic and Cardiovascular Surgery*, vol. 97, No. 2, pp 194–203, Feb. 1989.

P. Knoringer, "Fibrin Sealing in Spinal Neurosugery", 1986.

P. M. McCarthy, et al., "Fabrin Sealant: The Cleveland Clinic Experience", 1991.

M. Dahan et al., "The Importance of Biological Glue for the Prevention of Air Leakage in Pulmonary Sugery", *Materials and Methods*, pp 113–116, 1991.

H.W. Walclawiczek, "Fibrin Sealing in Liver and Spleen Sugery", 1994.

C. Shaffrey, et al., "Neurosurgical Applications of Fibrin Glue: Augmentation of Dural Closure in 134 Patients", *Neurosurgery*, vol. 26, No.2, pp 207–210, 1990.

M. Acqui, R. Delfini, A. Raco, and L. Ferrante, "Our Experience with Human Fibrin Glue in Neurosurgical Procedures", date unknown.

Allan Hjortrup, M.D., Flemming Moesgaard, M.D., Ph.D., Johan Kjaergard, M.D., Ph.D, "Fibrin Adhesive in Perineal Fistulas", from the Dept of Surgical Gastroenterology F, Bispebjerg Hospital and Dept of Surgical Gastroenterology C, Rigsbospitalet, University of Copenhagen, Copenhagen, Denmark, vol. 34. No. 9, Sep. 1991.

T.M. Kieser, A. Maitland, L. Parsons, L. Davison, and R.C. Woodman, "Reduced Postoperative Bleeding Following Use of Tisseel Fibrin Sealant in 300 Patients Undergoing Open–Heart Surgery", date unknown.

William D. Spotnitz, M.D., and Rosanne L. Welker, Ph.D, "Clinical Uses of Fabrin Sealant", *Tranfusion Therapy: Clinical Principles and Practice*, Bethesda, MD: AABB Press, 1999.

N. Tajima, S. Kuwahara, S. Hirakawa, and K. Matsumoto, "Bone Grafts Using Fibrin Glue for Posterolateral Spinal Fusion and Total Hip Replacement with Central Migration", date unknown.

Bong Gyu Yu, et al., "Development of a local antibiotic delivery system using fibrin glue", *Journal of Controlled Release*, 39, pp 65–70 (1996).

Gregory E. Lutz, M.D., Vijay B. Vad, M.D., and Ronald J. Wisneski, M.D., "Flourscopic Transforaminal Lumbar Epidural Steroids: An Outcome Study", *Arch Phys Med Rehabil*, Vol 79, pp 18–21, Nov. 1998.

Goupille P, Jayson MI, Valat JP, Freemont AJ, "The Role of Inflammation in Disk Herniation–Associated Radiculopathy", *Semin Arthritis Rheum*, 1998, Aug. 28 (1):60–71.

Kang JD, Georgeescu HI, McIntyre–Larkin L, Stefanovic–Racic M, Donaldson WF $3^{rd}$, Evans CH, "Herinated Lumbar Intervertebral Disc Spontaneously Produce Matrix Metalloproteinases, Nitric Oxide, Interleukin–6, and Prostaglandin E2", *Spine* 1996 Feb 1; 21(3);271–70.

Saal JS, Franson RC, Dobrow R, Saal JA, White AH, Goldthwaite N, "High Levels of Inflammatory Phospholipase A2 Activity in Lumbar Disc Herniations", *Spine* 1990 Jul; 15 (7):674–8.

Nygaard OP, Mellgren SI, Osterud B, "The Inflammatory Properties of Contained and Noncontained Lumbar Disc Herniation", *Spine* Nov 1 1997;22(21):2484–88.

Takahashi H, Suguro T, Okazima Y, Motegi M, Okada Y, Kakiuchi T, "Inflammatory Cytokines in the Herniated Disc of the Lumbar Spine", *Spine* Jan 15 1996;21(2):218–24.

Product Information, Celestone Soluspan, brand of betamethasone sodium phosphate and betamethasone acetate Injectable Suspension, USP 6 mg per mL, Schering Corporation, Kenilworth, NJ 07033 USA, Rev. Mar. 1996.

Product Information, *Fibrin Sealant Hemaseel APR Kit, Two–Component Fibrin Sealant, Vapor Heated, Kit,* Manufactured for and Distributed by Haemacure Corp., 2 N. Tamiami Trail, Ste. 802, Sarasota, FL. 34236, Issued May 1998.

* cited by examiner

BIOLOGICAL BIOADHESIVE COMPOSITION AND METHODS OF PREPARATION AND USE

This application is a Continuation-In-Part of co-pending U.S. patent application Ser. No. 09/888,310, filed on Jun. 22, 2001, entitled "Biological Bioadhesive Composition and Methods of Preparation and Use", and issuing on Oct. 22, 2002 as U.S. Pat. No. 6,468,527, which claims priority from U.S. Provisional Patent Application Serial No. 60/213,806, filed on Jun. 22, 2000, entitled "Biological Bioadhesive Composition and Methods of Preparation and Use" the disclosures of which are both incorporated herein by this reference.

BACKGROUND OF THE INVENTION

1. Field of the Invention

The present invention relates generally to the preparation and use of biological tissue adhesives which rely on combining fibrinogen and thrombin. More particularly, the present invention relates to an improved fibrin sealant (FS) which incorporates various biological and/or non-biological agents into its composition. The invention further relates to a novel method of application for such a sealant whereby the sealant and accompanying agent(s) are delivered to discrete sites within the body and held in place due to the bio-static characteristics of the improved sealant.

2. Related Art

Fibrin sealants, and glues, are well known and are used extensively in various clinical settings. Such sealants are indicated as adjuncts to hemostasis in surgeries when control of bleeding by conventional surgical techniques, including suture, ligature, and cautery is ineffective or impractical. For instance, fibrin sealants have been shown to be effective in patients undergoing reoperative cardiac surgery (J. Rousou, et al., Journal of Thoracic and Cardiovascular Surgery, vol.97, no.2, pp 194–203, February 1989), spinal neurosurgery (P. Knoringer, *Fibrin Sealing in Spinal Neurosurgery*, 1986), general cardiac surgery (P. M. McCarthy, et al., *Fibrin Sealant: The Cleveland Clinic Experience*, 1991), pulmonary surgery, (M. Dahan et al., *The Importance of Biological Glue for the Prevention of Air Leakage in Pulmonary Surgery*, Materials and Methods, pp 113–116, 1991), liver and spleen surgery (H. W. Waclawiczek, *Fibrin Sealing in Liver and Spleen Surgery*, 1994), and neurosurgical procedures© Shaffrey, et al., Neurosurgery, vol.26, No.2, pp 207–210, 1990).

Use of fibrin glue and methods for its preparation and use are described by Hirsh et al. in U.S. Pat. No. 5,643,192. Hirsh discloses the extraction of fibrinogen and thrombin components from a single donor, and the combination of only these components for use as a fibrin glue. Marx, U.S. Pat. No. 5,651,982, describes another preparation and method of use for fibrin glue. Marx provides a fibrin glue with liposomes for use as a topical sealant in mammals. The preparation and use of a topical fibrinogen complex (TFC) for wound healing is known in the field. PCT Application No. PCT/US95/15876, PCT Publication No. WO96/17633, of The American Red Cross discusses TFC preparations containing fibrinogen, thrombin, and calcium chloride, for example, at pages 16–18 of PCT Publication No. WO96/17633.

Still, there remains a need for a tissue sealant that may be delivered to discrete sites within the body and that has the capacity to localize and mediate the release of drugs and/or other biological and non-biological agents, which may be embedded in the sealant composition.

SUMMARY OF THE INVENTION

In accordance with the objects of the present invention, an improved fibrin sealant (FS) is provided which incorporates various biological and non-biological agents into the sealant composition. The sealant preferably comprises, at its core, fibrinogen and thrombin components which are reconstituted in the presence of compounds such as drugs, chemicals, or proteins, which include, but are not limited to; antibiotics, anticoagulants, steroids, cardiovascular drugs, chemoattractants, local anesthetics, and antiproliferative or antitumor drugs. Additionally, a corticosteroid-containing solution such as, for example, a betamethasone solution containing betamethasone acetate or betamethasone sodium phosphate; a triamicinolone solution; or a methylprednisolone solution, among others, may be used to reconstitute the thrombin or fibrinogen components from a freeze-dried state. Previously, calcium chloride solutions have been used to reconstitute freeze-dried thrombin. The corticosteroid-containing solution of the present invention may be used in place of, or in conjunction with, the calcium chloride solutions of previous compositions. Fibrinogen is typically reconstituted from a freeze-dried state in an aprotinin solution. However, a corticosteroid, or a corticosteroid-containing mixture, may be provided to supplement this solution.

In addition to the improved sealant, a novel method of delivering said sealant to discrete sites within the body is disclosed. Using this method, the disclosed sealant may be employed as biological carrier for the introduction of various drugs, chemicals, or proteins into the body. When used as a carrier for drug delivery, or similar applications, the biostatic qualities of fibrin clots facilitate prolonged, localized delivery of various agents including, but not limited to, those selected from the previous list. In addition, the disclosed biological sealant is biodegradable and may be formulated to minimize or eliminate immunogenicity problems and adverse foreign body reactions thereby providing superior therapeutic benefit to patients.

DETAILED DESCRIPTION OF THE INVENTION

Figure 1:
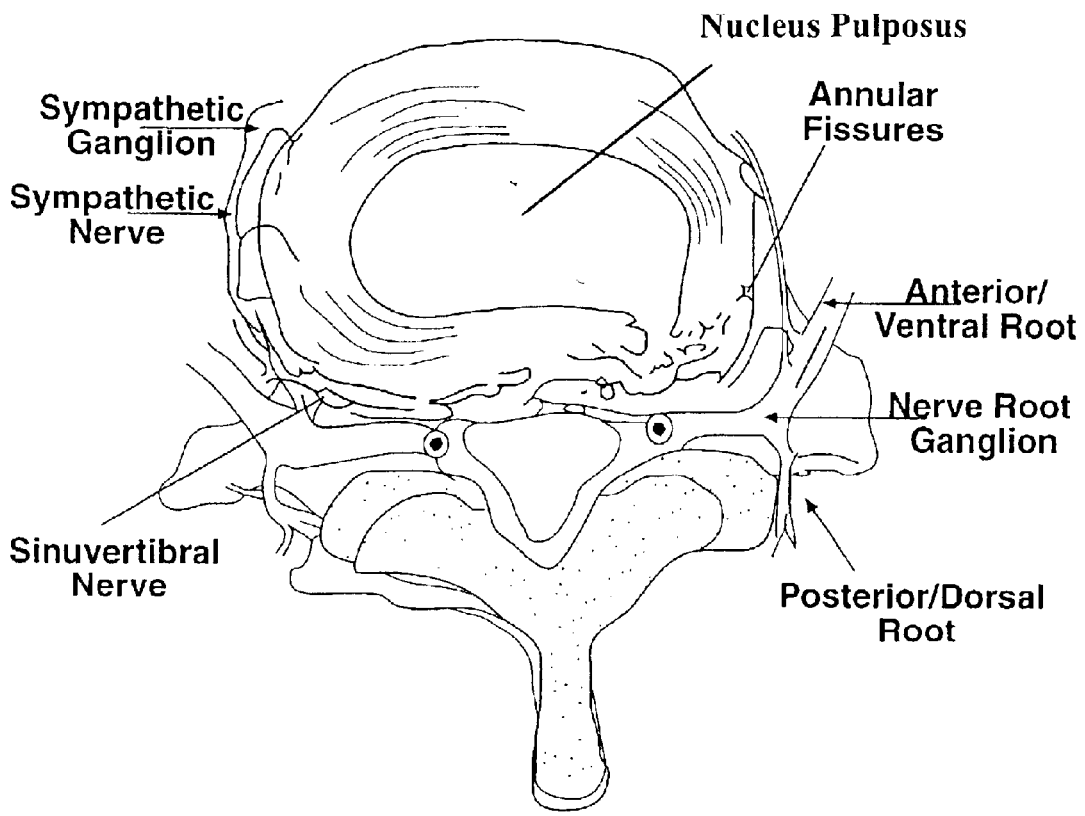
FIG. 1 is a cross-sectional view of a vertebral body at the disk space exhibiting annular fissures which may be treated according to one embodiment of the present invention.
Figure 2:
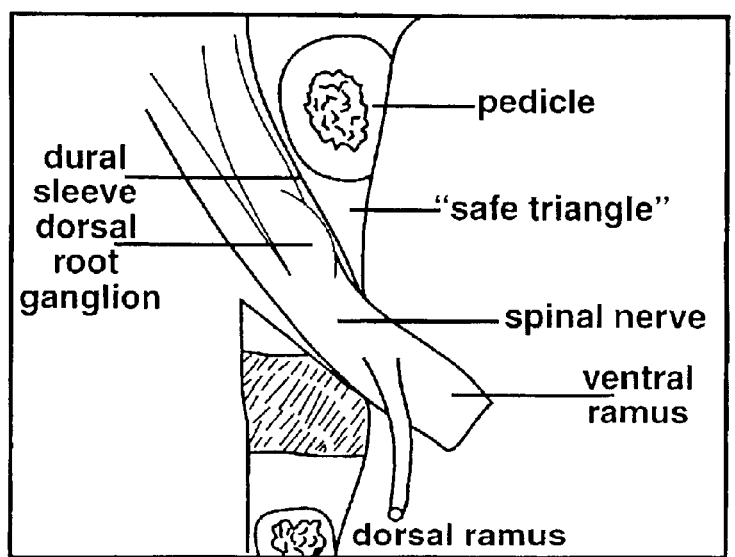
FIG. 2 is a schematic representation of the trans-foraminal space into which the improved sealant may be injected according to one embodiment of the present invention.

The present invention is an improved fibrin sealant (FS) composition which facilitates localized delivery of various biological and non-biological agents, such as drugs, chemicals, and proteins, to discrete locations within the body. The disclosed sealant exploits the biological adhesive qualities of fibrin sealant to restrict the administration of the desired agents to very particular sites when necessary. Further, the bio-static characteristics of the FS permit modulation of drug release over time.

The fibrin sealant of the present invention comprises preferably a fibrinogen component, a thrombin component, and a corticosteroid-containing solution such as, for example, a betamethasone solution containing betamethasone acetate or betamethasone sodium phosphate; a triamicinolone solution; or a methylprednisolone solution. The corticosteroid-containing solution of the present invention may be used as a substitute for, or a complement to, calcium chloride solutions previously known and used for reconstituting thrombin from a freeze-dried state. It is also foreseeable that a corticosteroid, or corticosteroid-containing solution, may be incorporated into the aprotinin solution which is used to reconstitute fibrinogen. Additional components may be added to the sealant such as, but not limited to: antibiotics; antiproliferative/cytotoxic drugs; antivirals; cytokines; colony stimulating factors; erythropoietin; antifungals; antiparasitic agents; anti-inflammatory agents; steroids; anesthetics; analgesics; oncology agents; and hormones. Other compounds which may added to the FS include, but are not limited to: vitamins and other nutritional supplements; hormones; glycoproteins; fibronectin; peptides and proteins; carbohydrates; proteoglycans; antiangiogenins; antigens; oligonucleotides; BMPs; DBM; antibodies; and gene therapy reagents. Genetically altered cells, stem cells, and/or other cells may also be included in the sealant. For some applications, cell growth factors may also be added to the composition to promote rehabilitation of damaged tissue and/or growth of new, healthy tissue. Preferably, oxygen-containing components; enzymes such as, for example, peroxidase, which mediate the release of oxygen from such components; nutrients such as, for example, glucose; and other cells are provided with growth factors to accelerate healing and growth. However, it is foreseeable that any of these components may be added to the invented FS separately. The oxygen-containing supplements are especially relevant in low-oxygen environments such as, for example, within spinal discs.

Fibrin sealants mimic the final stage of the natural clotting mechanism. Typically, such sealants entail the mixing of a fibrinogen component with an activating enzyme such as thrombin. Thrombin is an enzyme that exists in blood plasma which causes the clotting of blood by converting fibrinogen into fibrin. In normal practice, the components of the FS are reconstituted separately, from a freeze-dried state, prior to use. However, the use of samples prepared from a frozen state or a fresh state is also acceptable. To increase biocompatibility of the sealant with host tissue, various components may be supplied endogenously from host body fluids. Combining the reconstituted components produces a viscous solution that quickly sets into an elastic coagulum. A method of preparing a conventional fibrin sealant is described by J. Rousou, et al. in the Journal of Thoracic and Cardiovascular Surgery, vol.97, no.2, pp 194–203, February 1989. Cryoprecipitate derived from source plasma is washed, dissolved in buffer solution, filtered and freeze-dried. The freeze-dried fibrinogen is reconstituted in a fibrinolysis inhibitor solution containing, for example 3000 KIU/ml of aprotinin (a polyvalent protease inhibitor which prevents premature degradation of the formed fibrin). The solution is stirred and heated to a temperature of about 37° C. This solution must be used within four hours, or discarded. Freeze-dried thrombin is reconstituted in a calcium chloride solution. The solution is stirred until the thrombin is fully dissolved and maintained at a temperature of 37° C. Each solution is drawn up in a syringe and mounted on a Y-connector to which a needle is attached for delivery of the combined solution. (See, e.g. the Duploject® device, from ImmunoAG, Vienna, Austria). Thus, mixing of the components only occurs during the delivery process which facilitates clot formation at the desired site of application only. Fibrin sealant, prepared in the above described manner, is typically used for a variety of topical applications. Another previously known method of tissue sealant preparation, for topical wounds, may be found on pages 36–38 of PCT Application No. PCT/US95/15876, PCT Publication No. WO96/17633, by The American Red Cross.

The present invention is an improvement upon existing sealant technologies in that the fibrinogen, or thrombin, components may be reconstituted in the presence of various biological or non-biological agents. For the reconstitution of the thrombin, these biological or nonbiological agents may be used instead of, or in addition to calcium chloride. For the reconstitution of fibrinogen, these agents may be provided in addition to the aprotinin solution which is previously known in the art. This way, treatment agents are embedded in the FS composition and the sealant becomes a vehicle for the delivery of these compounds to discrete sites within the body. In addition, compounds which stabilize or extend the longevity of the fibrin sealant may be added to the mixture. Generally, these compounds are poorly soluble in water. Therefore, such compounds may increase the duration of drug, or similar agent, release from the FS and enhance the ability of the sealant to deliver localized dosages.

Preferably, the final mixing of the FS components occurs in a needle mounted on a Y-connector which connects a dual syringe system. This method of preparation facilitates the formation of a clot at the desired site during delivery, or immediately thereafter. The agent(s) chosen depend upon the indications of the particular patient and the specific application. These agents are typically treatment agents such as drugs. For example, in a preferred embodiment, a corticosteroid-containing solution such as, for example, a betamethasone solution containing betamethasone acetate or betamethasone sodium phosphate; a triamicinolone solution; or a methylprednisolone solution is used to reconstitute the thrombin from its freeze-dried state. The addition of a calcium chloride to the reconstitution mixture is desirable because it appears to improve the durability of the final clot. Freeze-dried fibrinogen is reconstituted according to conventional means and the individual FS components are loaded into the separate receivers of the Y-connector for subsequent injection. Fibrin sealants of this type may be used to treat various back injuries such as degenerative disc and incompetent disc diseases.

Addition of a corticosteroid treatment agent to freeze-dried preparations is generally preferred, but a corticosteroid treatment agent may also be added to fresh fibrinogen or thrombin (for example, separated from materials freshly removed from a patient's own body), or added to thawed/frozen or to-be-frozen fibrinogen or thrombin. Frozen or fresh, as opposed to freeze-dried, fibrinogen and/or thrombin components, therefore, may be used in some instances, and the addition of the preferred corticosteroid and calcium chloride solution to the thawed/frozen or fresh fibrinogen and/or thrombin, or the addition of said solution to fibrinogen and/or thrombin before freezing of the fibrinogen or thrombin, is not "reconstituting," and so the terms "mixing" or "adding" are used instead. Frozen or fresh thrombin or fibrinogen samples are not expected to require supplementation with calcium chloride because fresh-handling or freeze-handling of such samples preserves the calcium chloride that is naturally present in blood.

In an especially-preferred embodiment, about 75–105 mg/mL of freeze-dried fibrinogen is reconstituted according to conventional methods, arid about 45–55 mg/mL thrombin component is reconstituted separately from a freeze-dried state according to the methods and compositions of the present invention. Freeze-dried fibrinogen and freeze-dried thrombin are available in kit-form from such manufacturers as Baxter under names such as Tisseel® These two FS components are preferably prepared in about 2 mL samples each to yield approximately 4 mL of total sealant (reconstituted fibrinogen plus reconstituted thrombin).

While several methods and compositions may be used for preparing the freeze-dried thrombin for use in the invented FS, the preferred method is providing about 45–55 mg/mL of freeze-dried thrombin and mixing it with a reconstituting solution, wherein the reconstituting solution comprises about 4–12 milligrams of either 1) only betamethasone sodium phosphate, 2) only betamethasone acetate, or 3) a blend of the two, dissolved in about 2 mL of acqueous calcium chloride solution with a calcium chloride concentration of generally between 4 and 40 millimoles/mL. While the preferred calcium chloride concentration is 4–40 millimoles/mL, an even broader range may be appropriate, for example, 1–100 millimoles/mL. The calcium chloride concentration should be sufficient to further the polymerization reaction that forms a durable FS clot, and the inventor's believe that even a small concentration such as 1–4 millimoles/mL calcium chloride will provide sufficient calcium ions. A preservative-free reconstituting solution may be desirable, but is not required.

The concentration of calcium chloride in reconstituting solutions is preferably lower for solutions containing betamethasone sodium phosphate because the solubility of this compound appears to be reduced in the presence of aqueous calcium chloride. For such solutions, a calcium chloride concentration of about 4 millimoles/mL has been shown to produce adequate suspension without the need of an anti-caking agent. For solutions containing betamethasone acetate, an anti-caking agent such as, for example, polysorbate, may be added to facilitate suspension of this betamethasone component, which is otherwise highly insoluble. Glycol may be inappropriate for use as an anti-caking agent in the instant invention; however, polysorbate has been shown to be compatible with the instant invention. Blended betamethasone sodium phosphate and acetate solutions preferably include anti-caking agent(s) and low calcium chloride concentration(s).

Alternative amounts and concentrations of fibrinogen and thrombin may be used to form the desired FS clot in the body. For example, varying the fibrinogen and/or thrombin amount/concentration may be done to vary the viscosity and the "setting time" of the combined fibrinogen and thrombin components. Varying fibrinogen may change the density of the combined components, which may be important for controlling flow through a long conduit such as a catheter into the body. Varying thrombin may vary the polymerization time of the components, which may be important for controlling the time at which the clot forms for ensuring the components set-up at the proper site and time in the body rather than setting-up prematurely.

Preferably, the thrombin reconstituting solution, with the desired components, is prepared in a single vial prior to mixing with the freeze-dried thrombin. This component of the invented FS may then be provided to users in a reconstituted state, or in two uncombined vials containing freeze-dried thrombin and a premixed reconstitution solution. Mixing of the contents of the two vials may be performed at any point up to, and including, the time at which the improved FS is injected into the patient. The improved sealant may be used in a variety of applications. However, the improved FS finds particular application to the treatment of complications involving the back and/or spine. Therapeutic spinal injections to treat low back pain and sciatica are common in the field. For example, the use of corticosteroid injections into the lumbar epidural space for treatment of low back pain and radicular leg pain is known. It has been found that corticosteroids, such as betamethasone sodium phosphate and betamethasone acetate effectively reduce inflamation of the nerve root(s) and relieve associated pain symptoms. Therefore, use of a corticosteroid-containing solution in place of, or as a complement to, the calcium chloride solution, which is typically used to reconstitute freezedried thrombin in fibrin sealants may provide therapeutic value to sufferers of back pain. Additionally, the improved FS may be effective in treating degenerative and incompetent disc diseases. For the treatment of back injuries such as these, the improved FS is injected into the nucleus pulposus, shown in FIG. 1, to fill any fissures or voids, to seal the bone end plates to the disc, and to increase the height of the disc space. Sealing the fissures and bone end plates halts the leakage of harmful chemicals into the disc environment and prevents the initiation of foreign-body reactions towards the damaged disc by the immune system. Increasing the disc space relieves pressure from the nerve root. For this application, supplementation of the FS with growth factors may promote rehabilitation of the damaged tissues or the gradual replacement of the FS with healthy tissue.

To prepare the improved FS for such applications, reconstitution of the fibrinogen solution is accomplished according to conventional methods, as described above. Alternatively, the fibrinogen component may be reconstituted in an aprotinin solution which contains treatment agent(s) such as, for example, a corticosteroid. All solutions are brought to a temperature of about 37° C. Preferably, the thrombin and corticosteroid mixture is combined with the fibrinogen solution using the dual-syringe procedure described above to form a single sealant composition which is infused with a therapeutic biological agent, or agents. The embedded agent may be a corticosteroid such as, for example, betamethasone acetate or betamethasone sodium phosphate; triamicinolone; or methylprednisolone. Infusing the sealant composition with other agents may also be possible. The instant invention provides a vehicle for the delivery of the corticosteroid that conveys the corticosteroid to the precise area of inflammation and holds it in place via the elastic coagulum. In addition, the biodegradable nature of the formed fibrin clot minimizes or eliminates the need for invasive surgical removal following the effective period of use. Therefore, a distinct advantage of the improved sealant and method of application is the ability to provide a minimally invasive means of accomplishing localized, prolonged, and time-released drug delivery. The present invention may also have some of the advantages proposed for a wound-healing topical fibrinogen complex on pages 22 and 23 of PCT Application No. PCT/US95/15876, PCT Publication No. WO96/17633, by The American Red Cross.

Further advantages of the improved fibrin sealant may be realized in treatments such as, for example, fluoroscopic transforaminal epidural injection and intra-discal injection. Use of the improved FS composition may be better understood by reference to the following examples.

EXAMPLE 1

Fluoroscopic Transforaminal Epidural Injection

With the patient in the prone position on the imaging table, the fluoroscope is positioned and adjusted to locate the intervertebral foramen of the affected nerve root. A curved 22 ga. X 3.5" needle is introduced after anesthetizing the skin and deep tissue. The needle is advanced under direct fluoroscopic vision to a position in the anterior epidural space. Positioning of the needle is verified by a lateral fluoroscopic view and by injecting contrast medium through the needle. Such positioning may or may not require further adjustment. If adjusted, location of the needle is once again verified. Advancement of the needle into the correct region may stimulate pain in a manner consistent with the initial complaint. Therefore, needle placement may also be verified by the patient's pain recognition. The epidural space is anesthetized with injectable anesthetic. The improved fibrin sealant with the accompanying corticosteroid is then introduced through the needle with continuous gentle pressure until the volumes of the dual syringe system are sufficiently depleted. The FS then coats the nerve root and annulus and the needle is withdrawn. Patient observation and vital signs monitoring is usually performed for about 20–30 minutes following the procedure. Patients are then typically given routine discharge instructions and asked to call the following day. Patients may return for an evaluation within seven days.

For this procedure, a sufficient volume of the improved fibrin sealant is injected to effectively hydro-dissect the area around the targeted nerve root. The FS acts to hold the accompanying corticosteroid in place on the nerve root. It is believed that due to the avascular nature of the epidural space, the absorption/degradation period is typically longer than that observed for open applications in regions with greater vascularity and exposure to room air at the time of application. This phenomenon allows the corticosteroid to remain at the site of application longer, which prolongs its anti-inflammatory effect on the nerve root and surrounding tissue.

The ability of the fibrin sealant to seal annular fissures related to disc herniation offers a further therapeutic benefit to patients. Chemical radiculitis, or inflammation of the nerve root, is known to be quite painful in some instances. Corticosteroids have been shown to inhibit prostaglandin synthesis and impair the cell-mediated and humoral immune responses. It is believed that use of the improved FS in the above described manner not only coats the nerve root, but also seals annular fissures surrounding the herniated disk. (See FIG. 1). As a result of the hydro-dissection of the area around the affected nerve root, the improved sealant also seals annular fissures from outside the annulus.

Use of fibrin sealant on the dura, as a sealant, has been demonstrated to be effective as described in the study done at the University of Virginia Neurosurgery Department (C. Shaffrey, et al., Neurosurgery, vol.26, No.2, pp 207–210, 1990). This study validates the use of FS for its sealing capabilities rather than its hemostatic qualities, which shows that such sealants are multi-functional. For instance, fibrin sealants may: (1) seal and protect exposed nerve roots from further chemical damage, and (2) act as a vehicle to maintain corticosteroids in a lasting deposition on the nerve root. Furthermore, FS may be used to seal off the source of the chemical leakage to protect the nerve root from further chemical impairment. The improved fibrin sealant of this invention acts to maintain extended anti-inflammatory response to the corticosteroid and to seal the annular fissures that might otherwise permit the escape of damaging chemicals from the disc space. Exposure of the nerve root to such damaging chemicals may result in chemical radiculitis.

Patients who have been treated in this manner have had remarkable pain resolution within 24 to 48 hours. In some instances, further steroid injections have been necessary at other pain generator sites which had previously been masked by more prominent pain recognition in the region of the leaking disc. Multiple lesions at various levels are quite common.

EXAMPLE 2

Fluoroscopic Guided Intra-Discal Injection

After sterile preparation, an introduced needle is advanced in oblique projection to a superior articular process. A curved spinal needle is advanced through the introducer needle into the disc. Both anterior-posterior and lateral fluoroscopic projections are used to confirm proper needle placement. If the needle placement needs to be adjusted, placement is again confirmed fluoroscopically. Contrast is injected to confirm needle placement. In patients with chemical radiculitis, the contrast agent can be observed to be leaking through the annular fissures and/or intradiscal pathology can by identified. Once the needle is properly positioned in the intra-discal space, the improved fibrin sealant is injected. The FS is observed to force the contrast agent from the intra-discal space as it seals the annular fissures. The procedure not only soothes the nerve root and reduces inflamation, but also stops the chemical leakage and facilitates regeneration within the disc.

The foregoing examples are meant to illustrate certain aspects of carrying out the invention and are not intended to limit the scope of the invention in any way.

It is envisioned that the present invention may be used to address various conditions through use of the improved FS in a manner similar to that described in the examples above. For instance, it is foreseeable that harvested cartilage may be used to grow cells which may be injected in a manner similar to that above at implicated sites such as knee and elbow joints. The improved FS may be injected under the periosteum at the critical site. The improved sealant acts to seal the accompanying cells at the critical site. In the same manner, disc cells may be generated and injected intra-discally in the manner described above.

It is also envisioned that the improved FS of the present invention may be used to aid in facile recovery from radical breast mastectomy. In has been observed that after lymph nodes are removed, lymph fluid continues to leak post-operatively. The FS of the present invention may be reconstituted with critical chemotherapy agents and used to deliver said agents to, and seal, the critical site, thereby preventing further leakage while holding the chemotherapy agent in place.

It is also envisioned that the present invention may be used to deliver and seal in place suspended antibiotics, gene therapy agents, cell growth agents, analgesics, and replicated cell suspensions at various critical sites within the body.

Discussion of this invention referenced particular means, materials and embodiments elaborating limited application of the claimed invention. The invention is not limited to these particulars and applies to all equivalents.

Although this invention has been described above with reference to particular means, materials and embodiments, it is to be understood that the invention is not limited to these disclosed particulars, but extends instead to all equivalents within the scope of the following claims.

We claim:

1. A biological tissue adhesive for injection into a human body, the tissue adhesive comprising combined fibrinogen and thrombin, and a corticosteroid treatment agent.

2. A biological tissue adhesive as in claim 1, wherein a solution containing said corticosteroid treatment agent is added to said thrombin prior to combining the fibrinogen and the thrombin.

3. A biological tissue adhesive as in claim 2, wherein said solution is used to reconstitute the thrombin from a freeze-dried state.

4. A biological tissue adhesive as in claim 2, wherein said solution is added to thrombin prior to freezing said thrombin.

5. A biological tissue adhesive as in claim 2, wherein said solution is added to thrombin thawed from a frozen state.

6. A biological tissue adhesive as in claim 1, wherein a solution containing said corticosteroid treatment agent is added to the fibrinogen prior to combining the fibrinogen and the thrombin.

7. A biological tissue adhesive as in claim 6, wherein said solution is used to reconstitute the fibrinogen from a freeze-dried state.

8. A biological tissue adhesive as in claim 6, wherein said solution is added to the fibrinogen prior to freezing the fibrinogen.

9. A biological tissue adhesive as in claim 6, wherein said solution is added to fibrinogen thawed from a frozen state.

10. A biological tissue adhesive as in claim 1, wherein said solution further comprises calcium chloride.

11. A biological tissue adhesive as in claim 10, wherein the corticosteroid treatment agent comprises betamethasone.

12. A biological tissue adhesive as in claim 11, wherein the betamethasone comprises betamethasone sodium phosphate.

13. A biological tissue adhesive as in claim 11, wherein the betamethasone comprises betamethasone acetate.

14. A biological tissue adhesive an in claim 10, wherein the corticosteroid treatment agent comprises triamicinolone.

15. A biological tissue adhesive as in claim 10, wherein the corticosteroid treatment agent comprises methylprednisolone.

16. A biological tissue adhesive for injection into a human body, the tissue adhesive comprising combined fibrinogen and thrombin, wherein at least one of the fibrinogen and thrombin is mixed, prior to combination of the fibrinogen and thrombin, with a solution comprising corticosteroid treatment agent and calcium chloride.

17. A biological tissue adhesive as in claim 16, wherein said solution is mixed with said thrombin prior to combining the fibrinogen and the thrombin.

18. A biological tissue adhesive as in claim 17, wherein said solution is used to reconstitute the thrombin from a freeze-dried state.

19. A biological tissue adhesive as in claim 17, wherein said solution is mixed with the thrombin prior to freezing the thrombin.

20. A biological tissue adhesive as in claim 16, wherein a solution is added to the fibrinogen prior to combining the fibrinogen and the thrombin.

21. A biological tissue adhesive as in claim 20, wherein said solution is used to reconstitute the fibrinogen from a freeze-dried state.

22. A biological tissue adhesive as in claim 20, wherein said solution is mixed with the fibrinogen prior to freezing the fibrinogen.

23. A biological tissue adhesive comprising combined fibrinogen and thrombin and a corticosteroid treatment agent injected into biological tissue.

24. An adhesive as in claim 23, wherein said combined fibrinogen and thrombin and said corticosteroid treatment agent are injected into human biological tissue.

25. An adhesive as in claim 24, wherein said combined fibrinogen and thrombin and said corticosteroid are injected into a human spine nucleas pulposus.

26. An adhesive as in claim 23, wherein a solution containing said corticosteroid treatment agent is added to said thrombin prior to combining the fibrinogen and the thrombin.

27. An adhesive as in claim 26, wherein said solution is used to reconstitute the thrombin from a freeze-dried state.

28. An adhesive as in claim 26, wherein said solution is added to thrombin prior to freezing said thrombin.

29. An adhesive as in claim 26, wherein said solution is added to thrombin thawed from a frozen state.

30. An adhesive as in claim 23, wherein a solution containing said corticosteroid treatment agent is added to the fibrinogen prior to combining the fibrinogen and the thrombin.

31. An adhesive as in claim 30, wherein said solution is used to reconstitute the fibrinogen from a freeze-dried state.

32. An adhesive as in claim 30, wherein said solution is added to the fibrinogen prior to freezing the fibrinogem.

33. An adhesive as in claim 20, wherein said solution is added to fibrinogen thawed from a frozen state.

34. An adhesive as in claim 23, wherein said solution further comprises calcium chloride.

35. An adhesive as in claim 34, wherein the cortisteroid treatment agent comprises betamethasone.

36. An adhesive as in claim 35, wherein the betamethasone comprises betamethasone sodium phosphate.

37. An adhesive as in claim 35, wherein the betamethasone comprises betamethasone acetate.

38. An adhesive as in claim 34, wherein the corticosteroid treatment agent comprises triamicinolone.

39. An adhesive as in claim 34, wherein the corticosteroid treatment agent comprises methylprednisolone.

40. A biological tissue adhesive comprising fibrinogen and thrombin combined during injection into biological tissue, wherein at least one of the fibrinogen and thrombin is mixed, prior to combination of the fibrinogen and thrombin, with a solution comprising corticosteroid treatment agent and calcium chloride.

41. An adhesive as in claim 40, wherein said fibrinogen and thrombin are combined during injection into human biological tissue.

42. Ah adhesive as in claim 41, wherein said fibrinogen and thrombin are combined during injection into a human spine nucleus pulposus.

43. A biological tissue adhesive as in claim 40, wherein said solution is mixed with said thrombin prior to combining the fibrinogen and thrombin.

44. A biological tissue adhesive as in claim 43, wherein said solution is used to reconstitute the thrombin from a freeze-dried state.

45. A biological tissue adhesive as in claim 43, wherein said solution ia mixed with the thrombin prior to freezing the thrombin.

46. A biological tissue adhesive as in claim 40, wherein said solution is mixed with the thrombin prior to freezing the thrombin.

47. A biological tissue adhesive as in claim 46, wherein said solution is used to reconstitute the fibrinogen from a freeze-dried state.

48. A biological tissue adhesive as in claim 46, wherein said solution is mixed with the fibrinogen prior to freezing the fibrinogen.

* * * * *

UNITED STATES PATENT AND TRADEMARK OFFICE
CERTIFICATE OF CORRECTION

PATENT NO. : 6,921,532 B1
DATED : July 26, 2005
INVENTOR(S) : Sam L. Austin et al.

It is certified that error appears in the above-identified patent and that said Letters Patent is hereby corrected as shown below:

Title page,
Item [54], Title, delete "COMPOSITION" and insert -- COMPOSITIONS. --.

Column 9,
Line 58, after "corticosteriod," insert -- treatment agent --.

Column 10,
Line 16, delete "20," and insert -- 30 --.
Line 40, delete "Ah," and insert -- an --.
Line 50, delete "ia," and insert -- is --.

Signed and Sealed this

Twenty-seventh Day of September, 2005

JON W. DUDAS
*Director of the United States Patent and Trademark Office*